(12) United States Patent
Venkatraman et al.

(10) Patent No.: US 8,999,364 B2
(45) Date of Patent: Apr. 7, 2015

(54) IMPLANTABLE ARTICLE, METHOD OF FORMING SAME AND METHOD FOR REDUCING THROMBOGENICITY

(75) Inventors: Subramanian Venkatraman, Singapore (SG); Yin Chiang Boey, Singapore (SG)

(73) Assignee: Nanyang Technological University, Singapore (SG)

( * ) Notice: Subject to any disclaimer, the term of this patent is extended or adjusted under 35 U.S.C. 154(b) by 1217 days.

(21) Appl. No.: 11/753,896

(22) Filed: May 25, 2007

(65) Prior Publication Data

US 2007/0299510 A1 Dec. 27, 2007
US 2012/0179242 A9 Jul. 12, 2012

Related U.S. Application Data

(63) Continuation-in-part of application No. 10/867,617, filed on Jun. 15, 2004, now abandoned.

(60) Provisional application No. 60/808,558, filed on May 26, 2006.

(51) Int. Cl.
| A61L 27/28 | (2006.01) |
| A61L 29/08 | (2006.01) |
| A61L 31/08 | (2006.01) |
| A61F 2/04 | (2013.01) |
| A61F 2/06 | (2013.01) |
| A61F 2/00 | (2006.01) |
| A61L 27/58 | (2006.01) |
| A61L 27/34 | (2006.01) |
| A61L 31/10 | (2006.01) |
| A61L 27/18 | (2006.01) |
| A61L 27/50 | (2006.01) |
| A61L 27/56 | (2006.01) |
| A61L 33/00 | (2006.01) |

(52) U.S. Cl.
CPC ............... *A61F 2/0077* (2013.01); *A61L 27/58* (2013.01); *A61L 29/08* (2013.01); *A61L 27/34* (2013.01); *A61L 31/10* (2013.01); *A61L 31/08* (2013.01); *A61L 2420/06* (2013.01); *A61L 2420/08* (2013.01); *A61F 2/06* (2013.01); *A61F 2210/0004* (2013.01); *A61L 27/18* (2013.01); *A61L 27/50* (2013.01); *A61L 27/56* (2013.01); *A61L 33/0011* (2013.01); *A61L 2400/18* (2013.01)

(58) Field of Classification Search
None
See application file for complete search history.

(56) References Cited

U.S. PATENT DOCUMENTS

| 4,173,689 A | 11/1979 | Lyman et al. |
| 4,334,327 A | 6/1982 | Lyman et al. |
| 4,655,771 A | 4/1987 | Wallsten |
| 4,661,530 A | 4/1987 | Gogolewski et al. |
| 4,733,665 A | 3/1988 | Palmaz |
| 4,739,762 A | 4/1988 | Palmaz |
| 4,770,664 A | 9/1988 | Gogolewski |
| 4,776,337 A | 10/1988 | Palmaz |
| 4,834,747 A | 5/1989 | Gogolewski |
| 4,950,258 A | 8/1990 | Kawai et al. |
| 4,955,899 A | 9/1990 | Della Corna et al. |
| 5,061,275 A | 10/1991 | Wallsten et al. |
| 5,102,417 A | 4/1992 | Palmaz |
| 5,104,400 A | 4/1992 | Berguer et al. |
| 5,139,480 A | 8/1992 | Hickle et al. |
| 5,152,782 A | 10/1992 | Kowligi et al. |
| 5,163,952 A | 11/1992 | Froix |
| 5,258,020 A | 11/1993 | Froix |
| 5,288,711 A | 2/1994 | Mitchell et al. |
| 5,383,887 A | 1/1995 | Nadal |
| 5,421,955 A | 6/1995 | Lau et al. |
| 5,443,458 A | 8/1995 | Eury |
| 5,449,373 A | 9/1995 | Pinchasik et al. |
| 5,514,154 A | 5/1996 | Lau et al. |
| 5,516,781 A | 5/1996 | Morris et al. |
| 5,563,146 A | 10/1996 | Morris et al. |
| 5,607,467 A | 3/1997 | Froix |
| 5,630,162 A | 5/1997 | Wilkinson et al. |
| 5,630,840 A | 5/1997 | Mayer |
| 5,645,559 A | 7/1997 | Hachtman et al. |

(Continued)

FOREIGN PATENT DOCUMENTS

| CN | 10162971 | 1/2010 |
| DE | 4030998 | 4/1991 |

(Continued)

OTHER PUBLICATIONS

Eliaz et al., J. Biomed. Mater. Res., 2000, vol. 50:388-396.*

(Continued)

*Primary Examiner* — Xiaozhen Xie
(74) *Attorney, Agent, or Firm* — Levine Bagade Han LLP

(57) ABSTRACT

Endothelialization of a bodily fluid or tissue-contacting, particularly blood-contacting, surface may be accomplished to render that surface substantially non-thrombogenic. Thrombosis may also be mitigated or eliminated by providing an eroding layer on the surface that results in the removal of any thrombus formation as the layer erodes. An implantable device may utilize at least one surface having a plurality of nano-craters thereon that enhance or promote endothelialization. Additionally, an implantable device may have at least one first degradable layer for contacting bodily fluid or tissue and disposed about a central core, and at least one second degradable layer between the first degradable layer and the central core. The first degradable layer has a first degradation rate and the second degradable layer has a second degradation rate which degrades more slowly than the first degradable layer on contact with bodily fluid or tissue.

6 Claims, 4 Drawing Sheets

(56) References Cited

U.S. PATENT DOCUMENTS

| | | |
|---|---|---|
| 5,665,728 A | 9/1997 | Morris et al. |
| 5,670,161 A | 9/1997 | Healy et al. |
| 5,716,410 A | 2/1998 | Wang et al. |
| 5,733,303 A | 3/1998 | Israel et al. |
| 5,741,323 A | 4/1998 | Pathak et al. |
| 5,744,515 A | 4/1998 | Clapper |
| 5,769,816 A | 6/1998 | Barbut et al. |
| 5,795,318 A | 8/1998 | Wang et al. |
| RE35,988 E | 12/1998 | Winston et al. |
| 5,843,089 A | 12/1998 | Sahatjian et al. |
| 5,843,120 A | 12/1998 | Israel et al. |
| 5,848,987 A | 12/1998 | Baudino et al. |
| 5,922,021 A | 7/1999 | Jang |
| 5,935,164 A | 8/1999 | Iversen |
| 5,935,506 A | 8/1999 | Schmitz et al. |
| 5,954,744 A | 9/1999 | Phan et al. |
| 5,962,004 A | 10/1999 | Jannetta |
| 5,962,007 A | 10/1999 | Cooper et al. |
| 5,964,744 A | 10/1999 | Balbierz et al. |
| 5,972,018 A | 10/1999 | Israel et al. |
| 5,980,552 A | 11/1999 | Pinchasik et al. |
| 5,980,555 A | 11/1999 | Barbut et al. |
| 5,989,281 A | 11/1999 | Barbut et al. |
| 6,007,573 A | 12/1999 | Wallace et al. |
| 6,059,811 A | 5/2000 | Pinchasik et al. |
| 6,066,167 A | 5/2000 | Lau et al. |
| 6,086,605 A | 7/2000 | Barbut et al. |
| 6,090,097 A | 7/2000 | Barbut et al. |
| 6,090,134 A | 7/2000 | Tu et al. |
| 6,117,154 A | 9/2000 | Barbut et al. |
| 6,117,168 A | 9/2000 | Yang et al. |
| 6,136,016 A | 10/2000 | Barbut et al. |
| 6,153,252 A | 11/2000 | Hossainy et al. |
| 6,160,084 A | 12/2000 | Langer et al. |
| 6,168,619 B1 | 1/2001 | Dinh et al. |
| 6,217,815 B1 | 4/2001 | Sisbarro |
| 6,224,627 B1 | 5/2001 | Armstrong et al. |
| 6,231,326 B1 | 5/2001 | Sisbarro |
| 6,231,544 B1 | 5/2001 | Tsugita et al. |
| 6,235,045 B1 | 5/2001 | Barbut et al. |
| 6,248,129 B1 | 6/2001 | Froix |
| 6,254,632 B1 | 7/2001 | Wu et al. |
| 6,267,776 B1 | 7/2001 | O'Connell |
| 6,273,901 B1 | 8/2001 | Whitcher et al. |
| 6,281,262 B1 | 8/2001 | Shikinami |
| 6,309,412 B1 | 10/2001 | Lau et al. |
| 6,309,414 B1 | 10/2001 | Rolando et al. |
| 6,315,792 B1 | 11/2001 | Armstrong et al. |
| 6,322,847 B1 | 11/2001 | Zhong et al. |
| 6,331,188 B1 | 12/2001 | Lau et al. |
| 6,338,739 B1 | 1/2002 | Datta et al. |
| 6,338,793 B1 | 1/2002 | Putman |
| 6,364,904 B1 | 4/2002 | Smith |
| 6,379,383 B1 | 4/2002 | Palmaz et al. |
| 6,423,086 B1 | 7/2002 | Barbut et al. |
| 6,423,092 B2 | 7/2002 | Datta et al. |
| 6,432,133 B1 | 8/2002 | Lau et al. |
| 6,443,982 B1 | 9/2002 | Israel et al. |
| 6,461,381 B2 | 10/2002 | Israel et al. |
| 6,464,722 B2 | 10/2002 | Israel et al. |
| 6,485,511 B2 | 11/2002 | Lau et al. |
| 6,500,204 B1 | 12/2002 | Igaki |
| 6,503,270 B1 | 1/2003 | Richter et al. |
| 6,508,834 B1 | 1/2003 | Pinchasik et al. |
| 6,517,559 B1 | 2/2003 | O'Connell |
| 6,520,986 B2 | 2/2003 | Martin et al. |
| 6,530,950 B1 | 3/2003 | Alvarado et al. |
| 6,533,805 B1 | 3/2003 | Jervis |
| 6,533,808 B1 | 3/2003 | Thompson |
| 6,537,295 B2 | 3/2003 | Petersen |
| 6,537,311 B1 | 3/2003 | Cox et al. |
| 6,537,312 B2 | 3/2003 | Datta et al. |
| 6,540,774 B1 | 4/2003 | Cox |
| 6,540,775 B1 | 4/2003 | Fischell et al. |
| 6,540,776 B2 | 4/2003 | Sanders Millare et al. |
| 6,540,779 B2 | 4/2003 | Richter et al. |
| 6,544,279 B1 | 4/2003 | Hopkins et al. |
| 6,547,815 B2 | 4/2003 | Myers |
| 6,547,817 B1 | 4/2003 | Fischell et al. |
| 6,551,350 B1 | 4/2003 | Thornton et al. |
| 6,554,758 B2 | 4/2003 | Turnlund et al. |
| 6,554,858 B2 | 4/2003 | Dereume et al. |
| 6,562,063 B1 | 5/2003 | Euteneuer et al. |
| 6,562,065 B1 | 5/2003 | Shanley |
| 6,565,596 B1 | 5/2003 | White et al. |
| 6,565,598 B1 | 5/2003 | Lootz |
| 6,565,600 B2 | 5/2003 | Hojeibane |
| 6,565,602 B2 | 5/2003 | Rolando et al. |
| 6,575,887 B1 | 6/2003 | Schrayer |
| 6,575,994 B1 | 6/2003 | Marin et al. |
| 6,579,306 B1 | 6/2003 | Voelker et al. |
| 6,579,308 B1 | 6/2003 | Jansen et al. |
| 6,579,310 B1 | 6/2003 | Cox et al. |
| 6,582,447 B1 | 6/2003 | Patel et al. |
| 6,582,458 B1 | 6/2003 | White et al. |
| 6,582,467 B1 | 6/2003 | Teitelbaum et al. |
| 6,585,747 B1 | 7/2003 | Limon et al. |
| 6,585,757 B1 | 7/2003 | Callol |
| 6,589,264 B1 | 7/2003 | Barbut et al. |
| 6,589,266 B2 | 7/2003 | Whitcher et al. |
| 6,589,276 B2 | 7/2003 | Pinchasik et al. |
| 6,589,562 B1 | 7/2003 | Shefer et al. |
| 6,592,546 B1 | 7/2003 | Barbut et al. |
| 6,592,617 B2 | 7/2003 | Thompson |
| 6,596,021 B1 | 7/2003 | Lootz |
| 6,596,022 B2 | 7/2003 | Lau et al. |
| 6,599,308 B2 | 7/2003 | Amplatz |
| 6,602,279 B1 | 8/2003 | Nicholas |
| 6,605,107 B1 | 8/2003 | Klein |
| 6,605,110 B2 | 8/2003 | Harrison |
| 6,605,113 B2 | 8/2003 | Wilk |
| 6,607,501 B2 | 8/2003 | Gorsuch |
| 6,607,553 B1 | 8/2003 | Healy et al. |
| 6,613,073 B1 | 9/2003 | White et al. |
| 6,616,690 B2 | 9/2003 | Rolando et al. |
| 6,623,521 B2 | 9/2003 | Steinke et al. |
| 6,626,933 B1 | 9/2003 | Lau et al. |
| 6,626,934 B2 | 9/2003 | Blaeser et al. |
| 6,626,938 B1 | 9/2003 | Butaric et al. |
| 6,626,939 B1 | 9/2003 | Burnside et al. |
| 6,629,991 B1 | 10/2003 | Lau et al. |
| 6,635,082 B1 | 10/2003 | Hossainy et al. |
| 6,635,084 B2 | 10/2003 | Israel et al. |
| 6,652,558 B2 | 11/2003 | Patel et al. |
| 6,652,572 B2 | 11/2003 | Kugler et al. |
| 6,652,574 B1 | 11/2003 | Jayaraman |
| 6,652,575 B2 | 11/2003 | Wang |
| 6,652,579 B1 | 11/2003 | Cox et al. |
| 6,652,581 B1 | 11/2003 | Ding |
| 6,653,426 B2 | 11/2003 | Alvarado et al. |
| 6,656,219 B1 | 12/2003 | Wiktor |
| 6,656,220 B1 | 12/2003 | Gomez et al. |
| 6,666,883 B1 | 12/2003 | Seguin et al. |
| 6,669,722 B2 | 12/2003 | Chen et al. |
| D484,979 S | 1/2004 | Fontaine |
| 6,673,106 B2 | 1/2004 | Mitelberg et al. |
| 6,679,910 B1 | 1/2004 | Granada |
| 6,679,911 B2 | 1/2004 | Burgermeister |
| 6,685,736 B1 | 2/2004 | White et al. |
| 6,687,553 B2 | 2/2004 | Erickson et al. |
| 6,689,158 B1 | 2/2004 | White et al. |
| 6,689,159 B2 | 2/2004 | Lau et al. |
| 6,699,256 B1 | 3/2004 | Logan et al. |
| 6,699,276 B2 | 3/2004 | Sogard et al. |
| 6,699,278 B2 | 3/2004 | Fischell et al. |
| 6,702,844 B1 | 3/2004 | Lazarus |
| 6,702,846 B2 | 3/2004 | Mikus et al. |
| 6,702,850 B1 * | 3/2004 | Byun et al. .......... 623/1.44 |
| 6,706,062 B2 | 3/2004 | Vardi et al. |
| 6,709,425 B2 | 3/2004 | Gambale et al. |
| 6,709,453 B2 | 3/2004 | Pinchasik et al. |
| 6,709,454 B2 | 3/2004 | Cox et al. |
| 6,716,240 B2 | 4/2004 | Fischell et al. |
| 6,719,782 B1 | 4/2004 | Chuter |

(56) References Cited

U.S. PATENT DOCUMENTS

| | | | |
|---|---|---|---|
| 6,719,934 | B2 | 4/2004 | Stinson |
| 6,736,842 | B2 | 5/2004 | Healy et al. |
| 6,740,114 | B2 | 5/2004 | Burgermeister |
| 6,746,476 | B1 | 6/2004 | Hojeibane |
| 6,752,829 | B2 | 6/2004 | Kocur et al. |
| 6,753,071 | B1 | 6/2004 | Pacetti |
| 6,756,094 | B1 | 6/2004 | Wang et al. |
| 6,758,858 | B2 | 7/2004 | McCrea et al. |
| 6,758,859 | B1 | 7/2004 | Dang et al. |
| 6,758,860 | B1 | 7/2004 | Penn et al. |
| 6,764,506 | B2 | 7/2004 | Roubin et al. |
| 6,764,507 | B2 | 7/2004 | Shanley et al. |
| 6,770,088 | B1 | 8/2004 | Jang |
| 6,770,089 | B1 | 8/2004 | Hong et al. |
| 6,770,091 | B2 | 8/2004 | Richter et al. |
| 6,773,455 | B2 | 8/2004 | Allen et al. |
| 6,776,022 | B2 | 8/2004 | Kula et al. |
| 6,780,164 | B2 | 8/2004 | Bergheim et al. |
| 6,783,543 | B2 | 8/2004 | Jang |
| 6,783,544 | B2 | 8/2004 | Lynch et al. |
| 6,786,929 | B2 | 9/2004 | Gambale et al. |
| 6,790,226 | B2 | 9/2004 | Edwin et al. |
| 6,790,227 | B2 | 9/2004 | Burgermeister |
| 6,790,228 | B2 | 9/2004 | Hossainy et al. |
| 6,792,979 | B2 | 9/2004 | Konya et al. |
| 6,793,672 | B2 | 9/2004 | Khosravi et al. |
| 6,794,485 | B2 | 9/2004 | Shalaby et al. |
| 6,796,997 | B1 | 9/2004 | Penn et al. |
| 6,796,999 | B2 | 9/2004 | Pinchasik |
| 6,802,858 | B2 | 10/2004 | Gambale et al. |
| 6,805,705 | B2 | 10/2004 | Hong et al. |
| 6,805,706 | B2 | 10/2004 | Solovay et al. |
| 6,805,898 | B1 | 10/2004 | Wu et al. |
| 6,808,533 | B1 | 10/2004 | Goodwin et al. |
| 6,814,746 | B2 | 11/2004 | Thompson et al. |
| 6,814,748 | B1 | 11/2004 | Baker et al. |
| 6,814,749 | B2 | 11/2004 | Cox et al. |
| 6,818,013 | B2 | 11/2004 | Mitelberg et al. |
| 6,818,014 | B2 | 11/2004 | Brown et al. |
| 6,818,015 | B2 | 11/2004 | Hankh et al. |
| 6,833,153 | B1 | 12/2004 | Roorda et al. |
| 6,835,203 | B1 | 12/2004 | Vardi et al. |
| 6,846,323 | B2 | 1/2005 | Yip et al. |
| 6,849,086 | B2 | 2/2005 | Cragg |
| 6,855,125 | B2 | 2/2005 | Shanley |
| 6,855,162 | B2 | 2/2005 | Parodi |
| 6,858,037 | B2 | 2/2005 | Penn et al. |
| 6,860,898 | B2 | 3/2005 | Stack et al. |
| 6,860,901 | B1 | 3/2005 | Baker et al. |
| 6,860,946 | B2 | 3/2005 | Hossainy et al. |
| 6,863,685 | B2 | 3/2005 | Davila et al. |
| 6,866,805 | B2 | 3/2005 | Hong et al. |
| 6,875,228 | B2 | 4/2005 | Pinchasik et al. |
| 6,875,229 | B2 | 4/2005 | Wilson et al. |
| 6,881,223 | B2 | 4/2005 | Penn et al. |
| 6,884,258 | B2 | 4/2005 | Vardi et al. |
| 6,887,264 | B2 | 5/2005 | Penn et al. |
| 6,890,350 | B1 | 5/2005 | Walak |
| 6,893,458 | B2 | 5/2005 | Cox et al. |
| 6,896,697 | B1 | 5/2005 | Yip et al. |
| 6,896,699 | B2 | 5/2005 | Wilson et al. |
| 6,899,729 | B1 | 5/2005 | Cox et al. |
| 6,908,479 | B2 | 6/2005 | Lau et al. |
| 6,908,624 | B2 | 6/2005 | Hossainy et al. |
| 6,913,619 | B2 | 7/2005 | Brown et al. |
| 6,920,882 | B2 | 7/2005 | Berg et al. |
| 6,923,828 | B1 | 8/2005 | Wiktor |
| 6,932,832 | B2 | 8/2005 | Patel et al. |
| 6,932,930 | B2 | 8/2005 | DeSimone et al. |
| 6,935,404 | B2 | 8/2005 | Duerig et al. |
| 6,939,371 | B2 | 9/2005 | Kugler et al. |
| 6,942,689 | B2 | 9/2005 | Majercak |
| 6,945,949 | B2 | 9/2005 | Wilk |
| 6,949,117 | B2 | 9/2005 | Gambale et al. |
| 6,955,686 | B2 | 10/2005 | Majercak et al. |
| 6,955,687 | B2 | 10/2005 | Richter et al. |
| 6,955,688 | B2 | 10/2005 | Wilson et al. |
| 6,960,219 | B2 | 11/2005 | Grudem et al. |
| 6,960,228 | B2 | 11/2005 | Mitelberg et al. |
| 6,962,603 | B1 | 11/2005 | Brown et al. |
| 6,981,985 | B2 | 1/2006 | Brown et al. |
| 6,981,986 | B1 | 1/2006 | Brown et al. |
| 6,989,071 | B2 | 1/2006 | Kocur et al. |
| 6,991,642 | B2 | 1/2006 | Petersen |
| 6,991,647 | B2 | 1/2006 | Jadhav |
| 6,997,948 | B2 | 2/2006 | Stinson |
| 6,997,949 | B2 | 2/2006 | Tuch |
| 7,001,419 | B2 | 2/2006 | DiCaprio et al. |
| 7,001,424 | B2 | 2/2006 | Patel et al. |
| 7,004,966 | B2 | 2/2006 | Edwin et al. |
| D516,723 | S | 3/2006 | Shanley |
| 7,008,446 | B1 | 3/2006 | Amis et al. |
| 7,008,466 | B2 | 3/2006 | Collins |
| 7,011,672 | B2 | 3/2006 | Barbut et al. |
| 7,018,401 | B1 | 3/2006 | Hyodoh et al. |
| 7,029,492 | B1 | 4/2006 | Mitsudou et al. |
| 7,029,493 | B2 | 4/2006 | Majercak et al. |
| 7,037,331 | B2 | 5/2006 | Mitelberg et al. |
| 7,048,014 | B2 | 5/2006 | Hyodoh et al. |
| 7,052,513 | B2 | 5/2006 | Thompson |
| D523,558 | S | 6/2006 | Shanley |
| 7,060,088 | B1 | 6/2006 | Fischell et al. |
| 7,060,089 | B2 | 6/2006 | Ley et al. |
| 7,063,719 | B2 | 6/2006 | Jansen et al. |
| RE39,157 | E | 7/2006 | Hess |
| 7,070,617 | B2 | 7/2006 | Kula et al. |
| 7,081,130 | B2 | 7/2006 | Jang |
| 7,087,078 | B2 | 8/2006 | Hildebrand et al. |
| 7,094,255 | B2 | 8/2006 | Penn et al. |
| 7,097,652 | B2 | 8/2006 | Becker et al. |
| 7,100,617 | B1 | 9/2006 | Maginot |
| 7,101,392 | B2 | 9/2006 | Heath |
| 7,105,019 | B2 | 9/2006 | Hojeibane |
| 7,112,298 | B2 | 9/2006 | Kampa et al. |
| 7,118,593 | B2 | 10/2006 | Davidson et al. |
| 7,122,049 | B2 | 10/2006 | Banas et al. |
| 7,135,039 | B2 | 11/2006 | De Scheerder et al. |
| 7,137,993 | B2 | 11/2006 | Acosta et al. |
| 7,141,062 | B1 | 11/2006 | Pinchasik et al. |
| 7,147,649 | B2 | 12/2006 | Thomas |
| 7,160,592 | B2 | 1/2007 | Rypacek et al. |
| 7,166,125 | B1 | 1/2007 | Baker et al. |
| 7,169,170 | B2 | 1/2007 | Widenhouse |
| 7,169,173 | B2 | 1/2007 | Hossainy et al. |
| 7,169,174 | B2 | 1/2007 | Fischell et al. |
| 7,169,177 | B2 | 1/2007 | Obara |
| 7,172,623 | B2 | 2/2007 | Hansen et al. |
| 7,175,654 | B2 | 2/2007 | Bonsignore et al. |
| 7,179,286 | B2 | 2/2007 | Lenz |
| 7,179,288 | B2 | 2/2007 | Shanley |
| 7,195,648 | B2 | 3/2007 | Jones et al. |
| 7,204,847 | B1 | 4/2007 | Gambale |
| 7,204,848 | B1 | 4/2007 | Brown et al. |
| 7,208,010 | B2 | 4/2007 | Shanley et al. |
| 7,208,011 | B2 | 4/2007 | Shanley et al. |
| 7,214,240 | B2 | 5/2007 | Bonsignore et al. |
| 7,220,275 | B2 | 5/2007 | Davidson et al. |
| 7,226,558 | B2 | 6/2007 | Nieman et al. |
| 7,232,421 | B1 | 6/2007 | Gambale et al. |
| 7,252,679 | B2 | 8/2007 | Fischell et al. |
| 7,252,680 | B2 | 8/2007 | Freitag |
| 7,258,697 | B1 | 8/2007 | Cox et al. |
| 7,264,633 | B2 | 9/2007 | Bonsignore |
| 7,270,668 | B2 | 9/2007 | Andreas et al. |
| 7,288,111 | B1 | 10/2007 | Holloway et al. |
| 7,291,166 | B2 | 11/2007 | Cheng et al. |
| 7,294,146 | B2 | 11/2007 | Chew et al. |
| 7,294,214 | B2 | 11/2007 | Craig |
| 7,300,456 | B2 | 11/2007 | Andreas et al. |
| 7,311,726 | B2 | 12/2007 | Mitelberg et al. |
| 7,311,727 | B2 | 12/2007 | Mazumder et al. |
| 7,316,710 | B1 | 1/2008 | Cheng et al. |
| 7,316,711 | B2 | 1/2008 | Allen et al. |
| 7,320,702 | B2 | 1/2008 | Hammersmark et al. |

(56) References Cited

U.S. PATENT DOCUMENTS

| | | |
|---|---|---|
| 7,323,007 B2 | 1/2008 | Sano |
| 7,326,241 B2 | 2/2008 | Jang |
| 7,326,245 B2 | 2/2008 | Rosenthal et al. |
| 7,329,366 B1 | 2/2008 | Gale et al. |
| 7,331,984 B2 | 2/2008 | Tu et al. |
| 7,338,519 B2 | 3/2008 | Fischell et al. |
| 7,341,598 B2 | 3/2008 | Davidson et al. |
| 7,347,867 B2 | 3/2008 | Phelps et al. |
| 7,357,813 B2 | 4/2008 | Burgermeister |
| 7,572,287 B2 | 8/2009 | Stinson |
| 7,618,448 B2 | 11/2009 | Schmitz et al. |
| 8,206,635 B2 | 6/2012 | Ramzipoor et al. |
| 8,206,636 B2 | 6/2012 | Ramzipoor et al. |
| 2001/0014717 A1 | 8/2001 | Hossainy et al. |
| 2001/0029398 A1 | 10/2001 | Jadhav |
| 2001/0039432 A1 | 11/2001 | Whitcher et al. |
| 2002/0019661 A1 | 2/2002 | Datta et al. |
| 2002/0062134 A1 | 5/2002 | Barbut et al. |
| 2002/0077596 A1 | 6/2002 | McKenzie et al. |
| 2002/0077693 A1 | 6/2002 | Barclay et al. |
| 2002/0082682 A1 | 6/2002 | Barclay et al. |
| 2002/0143388 A1 | 10/2002 | Datta et al. |
| 2002/0165601 A1 | 11/2002 | Clerc |
| 2002/0169601 A1 | 11/2002 | Nishio |
| 2002/0188240 A1 | 12/2002 | Gorsuch |
| 2002/0193864 A1 | 12/2002 | Khosravi et al. |
| 2003/0031699 A1 | 2/2003 | Van Antwerp |
| 2003/0040771 A1 | 2/2003 | Hyodoh et al. |
| 2003/0040772 A1 | 2/2003 | Hyodoh et al. |
| 2003/0045924 A1 | 3/2003 | Datta et al. |
| 2003/0050678 A1 | 3/2003 | Sierra et al. |
| 2003/0050687 A1 | 3/2003 | Schwade et al. |
| 2003/0060836 A1 | 3/2003 | Wang et al. |
| 2003/0069629 A1 | 4/2003 | Jadhav et al. |
| 2003/0139765 A1 | 7/2003 | Patel et al. |
| 2003/0144730 A1 | 7/2003 | Datta et al. |
| 2003/0149475 A1 | 8/2003 | Hyodoh et al. |
| 2003/0153945 A1 | 8/2003 | Patel et al. |
| 2003/0157241 A1 | 8/2003 | Hossainy et al. |
| 2003/0163159 A1 | 8/2003 | Patel et al. |
| 2003/0176888 A1 | 9/2003 | O'Connell |
| 2003/0195628 A1 | 10/2003 | Bao et al. |
| 2003/0199918 A1 | 10/2003 | Patel et al. |
| 2003/0208227 A1 | 11/2003 | Thomas |
| 2003/0208259 A1 | 11/2003 | Penhasi |
| 2003/0216804 A1 | 11/2003 | DeBeer et al. |
| 2003/0225447 A1 | 12/2003 | Majercak et al. |
| 2004/0015187 A1 | 1/2004 | Lendlein et al. |
| 2004/0030377 A1 | 2/2004 | Dubson et al. |
| 2004/0033251 A1 | 2/2004 | Sparer et al. |
| 2004/0034403 A1 | 2/2004 | Schmitt |
| 2004/0034405 A1 | 2/2004 | Dickson |
| 2004/0047909 A1 | 3/2004 | Ragheb et al. |
| 2004/0086542 A1 | 5/2004 | Hossainy et al. |
| 2004/0113306 A1 | 6/2004 | Rapacki et al. |
| 2004/0127932 A1 | 7/2004 | Shah |
| 2004/0127970 A1 | 7/2004 | Saunders et al. |
| 2004/0127978 A1 | 7/2004 | Sparer et al. |
| 2004/0158276 A1 | 8/2004 | Barbut et al. |
| 2004/0162576 A1 | 8/2004 | Barbut et al. |
| 2004/0164030 A1 | 8/2004 | Lowe et al. |
| 2004/0170685 A1 | 9/2004 | Carpenter et al. |
| 2005/0004654 A1 | 1/2005 | Khosravi et al. |
| 2005/0004684 A1 | 1/2005 | Cribbs |
| 2005/0010170 A1 | 1/2005 | Shanley et al. |
| 2005/0010275 A1 | 1/2005 | Sahatjian et al. |
| 2005/0012171 A1 | 1/2005 | Hiyama et al. |
| 2005/0021131 A1* | 1/2005 | Venkatraman et al. ...... 623/1.19 |
| 2005/0038505 A1 | 2/2005 | Shulze et al. |
| 2005/0100577 A1 | 5/2005 | Parker et al. |
| 2005/0112171 A1 | 5/2005 | Tang et al. |
| 2005/0143817 A1 | 6/2005 | Hunter et al. |
| 2005/0154451 A1 | 7/2005 | Hezi-Yamit et al. |
| 2005/0154452 A1 | 7/2005 | Hezi-Yamit et al. |
| 2005/0154455 A1 | 7/2005 | Hezi-Yamit et al. |
| 2005/0177246 A1 | 8/2005 | Datta et al. |
| 2005/0187608 A1 | 8/2005 | O'Hara |
| 2005/0233061 A1 | 10/2005 | Schwarz |
| 2005/0254451 A1 | 11/2005 | Grosbach |
| 2005/0254455 A1 | 11/2005 | Plehn et al. |
| 2006/0020330 A1 | 1/2006 | Huang et al. |
| 2006/0024373 A1 | 2/2006 | Shahar et al. |
| 2006/0025852 A1 | 2/2006 | Armstrong et al. |
| 2006/0036316 A1 | 2/2006 | Zeltinger et al. |
| 2006/0041271 A1 | 2/2006 | Bosma et al. |
| 2006/0045901 A1 | 3/2006 | Weber |
| 2006/0051390 A1 | 3/2006 | Schwarz |
| 2006/0051394 A1 | 3/2006 | Moore et al. |
| 2006/0052859 A1 | 3/2006 | Igaki |
| 2006/0058832 A1 | 3/2006 | Melzer et al. |
| 2006/0058863 A1 | 3/2006 | LaFont et al. |
| 2006/0063316 A1 | 3/2006 | Yamagata et al. |
| 2006/0067974 A1 | 3/2006 | Labrecque et al. |
| 2006/0069427 A1 | 3/2006 | Savage et al. |
| 2006/0076708 A1 | 4/2006 | Huang et al. |
| 2006/0085062 A1 | 4/2006 | Lee et al. |
| 2006/0122522 A1 | 6/2006 | Chavan et al. |
| 2006/0122686 A1 | 6/2006 | Gilad et al. |
| 2006/0136043 A1 | 6/2006 | Cully et al. |
| 2006/0142736 A1 | 6/2006 | Hissink et al. |
| 2006/0147491 A1* | 7/2006 | DeWitt et al. ................ 424/426 |
| 2006/0149365 A1 | 7/2006 | Fifer et al. |
| 2006/0193891 A1 | 8/2006 | Richard |
| 2006/0212064 A1 | 9/2006 | Shah |
| 2006/0229660 A1 | 10/2006 | Pal et al. |
| 2006/0241675 A1 | 10/2006 | Johnson et al. |
| 2006/0241676 A1 | 10/2006 | Johnson et al. |
| 2006/0241677 A1 | 10/2006 | Johnson et al. |
| 2006/0241678 A1 | 10/2006 | Johnson et al. |
| 2006/0241679 A1 | 10/2006 | Johnson et al. |
| 2006/0241680 A1 | 10/2006 | Johnson et al. |
| 2006/0248871 A1 | 11/2006 | Johnson et al. |
| 2006/0259133 A1 | 11/2006 | Sowinski et al. |
| 2006/0287715 A1 | 12/2006 | Atladottir et al. |
| 2007/0032816 A1 | 2/2007 | O'Connell et al. |
| 2007/0038226 A1 | 2/2007 | Galdonik et al. |
| 2007/0038241 A1 | 2/2007 | Pal |
| 2007/0038290 A1 | 2/2007 | Huang et al. |
| 2007/0088383 A1 | 4/2007 | Pal et al. |
| 2007/0100430 A1 | 5/2007 | Rudakov et al. |
| 2007/0106361 A1 | 5/2007 | Epstein |
| 2007/0110889 A1 | 5/2007 | Sundar |
| 2007/0185561 A1 | 8/2007 | Schmitz et al. |
| 2007/0202046 A1 | 8/2007 | Dave |
| 2007/0250153 A1 | 10/2007 | Cully et al. |
| 2007/0281117 A1 | 12/2007 | Kaplan et al. |
| 2007/0283552 A1 | 12/2007 | Gale et al. |
| 2008/0051866 A1 | 2/2008 | Chen et al. |
| 2008/0091275 A1 | 4/2008 | Ducharme |
| 2008/0097620 A1 | 4/2008 | Venkatraman et al. |
| 2008/0103584 A1 | 5/2008 | Su et al. |

FOREIGN PATENT DOCUMENTS

| | | |
|---|---|---|
| EP | 0894505 | 2/1999 |
| EP | 0754017 | 6/2002 |
| EP | 1287790 | 3/2003 |
| EP | 1301221 B1 | 4/2003 |
| EP | 1372530 B1 | 1/2004 |
| EP | 1639962 A2 | 3/2006 |
| EP | 2322118 | 5/2011 |
| EP | 2355755 | 8/2011 |
| EP | 2493419 | 9/2012 |
| JP | 11-188110 | 7/1999 |
| JP | 2002-525166 | 8/2002 |
| JP | 2005-525170 | 8/2005 |
| JP | 2007-517587 | 7/2007 |
| JP | 2009-507528 | 2/2009 |
| WO | WO 97/17100 | 5/1997 |
| WO | WO 97/42879 | 11/1997 |
| WO | WO 98/46297 | 10/1998 |
| WO | WO 99/42528 | 8/1999 |
| WO | WO 99/65420 | 12/1999 |
| WO | WO 00/13737 | 3/2000 |

(56) References Cited

FOREIGN PATENT DOCUMENTS

| | | |
|---|---|---|
| WO | WO 00/18328 | 4/2000 |
| WO | WO 00/44308 | 8/2000 |
| WO | WO 00/66031 | 11/2000 |
| WO | WO 01/01886 | 1/2001 |
| WO | WO 01/10342 | 2/2001 |
| WO | WO 01/28454 | 4/2001 |
| WO | WO 02/11812 | 2/2002 |
| WO | WO 02/36045 | 5/2002 |
| WO | WO 02/076340 | 10/2002 |
| WO | WO 03/094796 | 11/2003 |
| WO | WO 2004/110315 | 12/2004 |
| WO | WO 2005/002646 | 1/2005 |
| WO | WO 2005/004249 | 1/2005 |
| WO | WO 2005/070335 | 8/2005 |
| WO | WO 2005/077303 | 8/2005 |
| WO | WO 2005/079301 | 9/2005 |
| WO | WO 2006/009883 | 1/2006 |
| WO | WO 2006/015161 | 2/2006 |
| WO | WO 2006/019634 | 2/2006 |
| WO | WO 2006/020425 | 2/2006 |
| WO | WO 2006/020616 | 2/2006 |
| WO | WO 2006/029012 | 3/2006 |
| WO | WO 2006/036982 | 4/2006 |
| WO | WO 2006/068981 | 6/2006 |
| WO | WO 2006/074163 | 7/2006 |
| WO | WO 2006/093608 | 9/2006 |
| WO | WO 2006/107939 | 10/2006 |
| WO | WO 2007/140320 | 12/2007 |

OTHER PUBLICATIONS

Tamai, Hideo et al, "Initial and 6-Month Results of Biodegradable Poly-*l*-Lactic Acid Coronary Stents in Humans." *Circulation*, 102(4): 399-404, Jul. 25, 2000.

De Scheerder et al., "Biocompatibility of polymer-coated oversized metallic stents implanted in normal porcine coronary arteries," *Atherosclierosis*, vol. 114(1) pp. 105-114, Apr. 7, 1995.

Kim et al., "Nonthrombogenic polymers: pharmaceutical approaches," *Am Soc Artif Intern Organs J*, vol. 6, pp. 76-87, 1983.

Kruzynska-Frejtag et al., "Periostin is expressed within the developing teeth at the sites of epithelial-mesenchymal interaction", *Dev. Dyn.*, vol. 229(4), pp. 857-868, Apr. 2004.

Merrill et al., "Properties of materials affecting the behavior of blood at their surfaces," *Ann NY Acad Sci*, vol. 283, pp. 6-16, Feb. 1977.

Petas et al., "Effects of biodegradable self-reinforced polyglycolic acid, poly-DL-lactic acid and stainless-steel spiral stents on uroepithelium after Nd:YAG laser irradiation of the canine prostate," *BR J. Urol.*, vol. 80(6), pp. 903-907, Dec. 1997.

Rafanan "Stenting of the tracheobronchial tree," *Radiol Clin North Am.*, vol. 38(2), pp. 395-408, Mar. 2000.

Schellhammer et al., "Poly-Lactic-Add Coating for Endovascular Stents: Preliminary Results in Canine Experimental Arteriovenous Fistulae [Preliminary Report]," *Invest Radiol.*, vol. 32(3), pp. 180-186, Mar. 1997.

Sofia Poly(Ethylene Glycol) Chemistry and Biological Applications, Ch. 22, pp. 342-360, *American Chemical Society*, vol. 680, Aug. 1997.

Szycher "Review of Cardiovascular Devices," *J. Biomat Appln*, vol. 12, pp. 321-364, 1998.

Tamai et al, "Initial and 6-Month Results of Biodegradable Poly-*l*-Lactic Acid Coronary Stents in Humans," *Circulation*, vol. 102(4), pp. 399-404, Jul. 25, 2000.

Webb et al., "Relative importance of surface wettability and charged functional groups on NIH 3T3 fibroblast attachment, spreading, and cytoskeletal organization", *J. Biomed Mat Res*, vol. 41(3), pp. 422-430, Sep. 5. 1998.

Tan et al., "Effect of plasticization on heparin release from biodegradable matrices", *Int. J. Pharm.*, vol. 283(102), pp. 89-96, Sep. 28, 2004.

\* cited by examiner

IMPLANTABLE ARTICLE, METHOD OF FORMING SAME AND METHOD FOR REDUCING THROMBOGENICITY

CROSS-REFERENCE TO RELATED APPLICATIONS

This application claims the benefit of priority to U.S. Provisional Patent Application No. 60/808,558, filed May 26, 2006; this application is also a continuation-in-part of U.S. Non-provisional patent application Ser. No. 10/867,617, filed Jun. 15, 2004 (now abandoned). The disclosure of all priority applications is incorporated herein by reference in their entirety.

FIELD OF THE INVENTION

The present invention relates generally to implantable devices, such as implantable medical devices, and methods for the manufacture thereof. The invention also relates to methods for enhancing and promoting endothelialization and for minimizing thrombus formation on the surface of the implantable device.

BACKGROUND OF THE INVENTION

In recent years there has been growing interest in the use of artificial materials, particularly materials formed from polymers, for use in implantable devices that come into contact with bodily tissues or fluids particularly blood. Some examples of such devices are artificial heart valves, stents and vascular prosthesis. Progress in this area has, however, been hampered somewhat by the thrombogenicity of many polymer materials. Reference is made to M. Szycher, *J. Biomat Appln* (1998) 12: 321 in that regard.

Efforts to overcome the problems associated with thrombogenicity of polymer materials used in the production of implantable devices have not met with a great deal of success to date. Some examples of approaches that have bee attempted include heparinization (S. W. Kim, C. D. Ebert, J. Y. Lin, J. C. McRea *Am Soc Artif Internal Organs* (1983) 6: 76), physical modification of the surface (K. Webb, W. Hlady, P. A Tresco, *J. Biomed Mat Res* (1998) 41: 421-430; E. W. Merrill, *Ann NY Acad Sci* (1977) 6: 283-290) and increasing surface hydrophilicity (S. J. Sofia, E. W. Merrill, in "Polyethylene Glycol; Chemistry and Biological Applications", J. M. Harris and S. Zalipsky (eds.), *American Chemical Society* (1997) Ch. 22). Although these methods have met with some commercial viability, they are mainly useful for short-term applications, such as in catheter or in dialysis tubing. This is because many of the chemical and physical modifications of the device surfaces have limited shelf-life, both ex vivo and in vivo. Moreover, the methods involved in the production of implantable devices using these approaches are both elaborate and intricate.

Attempts have also been made to minimize thrombus formation by promoting endothelialization of the surface of an implantable device that contacts bodily fluids or tissues in use as described, for example, in U.S. Pat. No. 5,744,515, which relates to modification of a porous material with adhesion molecules, and U.S. Pat. No. 6,379,383, which relates to deposition of the material used to form the device so as to control surface heterogenities.

SUMMARY OF THE INVENTION

Thrombus formation is a very complex process involving inter-dependent interactions between a surface of an implantable device, platelets and coagulation proteins. The present invention addresses the problem of thrombosis by endothelialization of a bodily fluid or tissue-contacting, particularly blood-contacting, surface to render that surface substantially non-thrombogenic. The invention also addresses the problem of thrombosis by providing an eroding layer on the surface that results in the removal of any thrombus formation as the layer erodes.

According to one aspect of the invention, there is provided an implantable device having at least one surface for contacting bodily fluid or tissue, said at least one surface comprising a plurality of nano-craters thereon that enhance or promote endothelialization of said at last one surface.

According to one aspect of the invention, there is provided an implantable device having at least one first degradable layer providing at least one surface of the implantable device for contacting bodily fluid or tissue and disposed about a central core, and at least one second degradable layer between said first degradable layer and the central core, wherein said first degradable layer has a first degradation rate and said second degradable layer has a second degradation rate such that said at least one first degradable layer degrades more rapidly than said at least one second degradable layer on contact with bodily fluid or tissue.

The material of the implantable device is not particularly limited. Furthermore, the nano-craters may be formed in the material that constitutes the body of the implantable device, or may be formed in a layer that is applied to a support substrate forming the implantable device. Generally, the nano-craters will be formed in a surface layer of suitable biocompatible material applied to a support structure for the implantable device. The options for the biocompatible material forming the outer layer of the implantable device are generally known and are discussed hereafter.

The form of the implantable device is similarly not particularly limited. This may include any device that is intended to come into contact with bodily fluids or tissues, be that during in vivo applications or in vitro applications. Examples of particular devices will be provided hereafter.

According to further aspect of the invention, there is provided a method of Manufacturing an implantable device having at least one surface for contacting bodily fluid or tissue comprising: providing on said at least one surface a plurality of nano-craters that enhance or promote endothelialization of said at least one surface.

According to a further aspect of the invention, there is provided a method of reducing thrombogenicity of an implantable device having at least one surface for contacting bodily fluid or tissue, or promoting or enhancing endothelialization of an implantable device having at least one surface for contacting bodily fluid or tissue, comprising: providing on said at least one surface a plurality of nano-craters that enhance or promote endothelialization of said at least one surface.

According to another aspect of the invention, there is provided a method of manufacturing an implantable device having at least one surface for contacting bodily fluid or tissue, comprising: providing at least one first degradable layer which provides said at least one surface and which is disposed about a central core, and at least one second degradable layer between said first degradable layer and the central core, wherein said first degradable layer has a first degradation rate and second degradable layer has a second degradation rate such that said at least one first degradable layer degrades more rapidly than said at least one second degradable layer on contact with bodily fluid or tissue.

According to still another aspect of the invention, there is provided a method of reducing thrombogenicity of an implantable device having at least one surface for contacting bodily fluid or tissue, comprising: providing at least one first degradable layer which provides said at least one surface and which is disposed about a central core, and at least one second degradable layer between said first degradable layer and the central core, wherein said first degradable layer has a first degradation rate and said second degradable layer has a second degradation rate such that said at least one first degradable layer degrades more rapidly than said at least one second degradable layer on contact with bodily fluid or tissue.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION OF THE INVENTION

Figure 1:
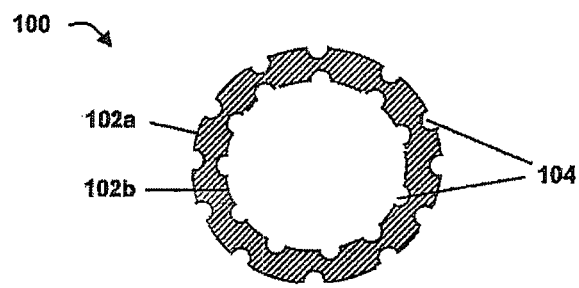
FIG. 1 is a schematic representation of an implantable device having nano-craters on the surface of the device.

When a bodily fluids-contacting or tissue-contacting, particularly blood-contacting, surface is coated with endothelial cells, it is rendered substantially non-thrombogenic. Thus, in one aspect, the reduced thrombogenicity of an implantable device is achieved by enhancing and/or promoting endothelialization of the surface of the implantable device that contacts bodily fluid or tissue.

This aspect of the invention is based on the surprising discovery that the inclusion of nano-craters on a surface of an implantable device that is intended to come into contact with bodily fluids or tissues, such as blood, advantageously improves endothelial cell attachment to the surface. The inclusion of the nano-craters therefore assists in the propagation of endothelial cells on the surface of the device. It is believed that the improved attachment and propagation of endothelial cells on the surface is a result of the nano-craters on the surface acting as foci for endothelial cell attachment. This aspect of the invention is particularly suited for manufacture of implantable devices that are intended to be in long-term contact with bodily fluids or tissues, particularly in long-term contact with blood.

In another aspect, the reduced thrombogenicity is achieved by providing a surface layer that degrades in a controlled fashion, such that any thrombus that is formed at the surface is removed as the surface layer degrades. This aspect of the invention is based on the discovery that by providing the surface with layers having different degradation rates, it is possible to remove any thrombus formed on the surface in a controlled fashion, by degradation of each successive layer. This aspect of the invention is particularly suited for manufacture of implantable devices that are intended to be in short-term contact with bodily fluids or tissues, particularly blood.

The implantable device described herein may be any device that would benefit from the reduced thrombogenicity of a surface, including by enhancement of the endothelialization of a surface or by degradation of surface that comes in contact with bodily fluid or tissue, as described below, so as to reduce or remove thrombus formation on such a surface, particularly where such a surface is a blood-contacting surface, when the device is in use.

As used herein, the term "implantable device", which may also be referred to as a "device" or a "medical device", refers to any device having at least one surface that comes in contact with bodily tissue or fluid, including blood, and includes a device for implanting in a subject's body, permanently or temporarily, long-term or short-term. The term, as used herein, also refers to any device that forms a part of an article.

It is envisaged that the device is useful not only for in vivo applications, but also in vitro applications. As such, the device is not particularly limited, but should be considered to include any device that is intended for contact with bodily fluids or tissues, particularly blood, including conduits, grafts, valves, dialysis tubing and stents. As used herein the term "bodily fluids or tissues" includes biologically derived fluids and tissues as well as synthetic substitutes, for example artificial blood.

As used herein, the term "endothelialization" refers to the growth and/or proliferation of endothelial cells on a surface, such as the blood-contacting surface, or an implantable device. Promoting or enhancing endothelialization of a surface refers to promoting, enhancing, facilitation or increasing the attachment of, and growth of, endothelial cells on the surface.

As would be appreciated by a skilled person, the surface of a device for implantation into a subject is preferably biocompatible. The term "biocompatible" means that a substance is minimally toxic or irritating to biological tissue, such as to be sufficiently tolerated in the body without adverse effect. The surface may be formed of a material, which is different from the material that forms the surface and which is used as a support. Alternatively, the device and surface may be formed of the same material.

Suitable materials for forming the surface include biostable polymers, for example, polyethylene, polyurethane, polyolefin, or polyethylene terephthalate and degradable polymers, including degradable by chemical means or by exposure to radiation, for example, poly-lactide (PLA) including poly-L-lactide (PLLA), poly-glycolide (PGA), poly(lactide-co-glycolide) (PLGA) or polycaprolactone. In certain other embodiments, the degradable polymer may be biodegradable, meaning that the substance will readily degrade in an environment that is, or that is equivalent to, the body of a subject, for example when in contact with bodily fluid or tissue.

Other suitable materials that can be used to form an implantable device, or to provide the surface of an implantable device, are generally known in the art and examples of such materials are outlined in U.S. Pat. No. 5,744,515, which is herein incorporated by reference. For example, preferred materials include synthetic polymers, including oligomers, homopolymers, and copolymers resulting from either addition or condensation polymerization. Examples of suitable addition polymers include, but are not limited to, acrylics such as those polymerized from methyl cerylate, methyl methacrylate, acrylic acid, methacrylic acid, acrylamide, hydroxyethyl acrylate, hydroxyethyl methacrylate, glyceryl scrylate, glyceryl methacrylate, methacrylamide and methacrylamide; vinyls such as styrene, vinyl chloride, binaly pyrrolidone, polyvinyl alcohol, and vinyls acetate; polymers formed of ethylene, propylene, and tetrafluoroethylene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketones.

Other suitable materials include metals and ceramics. The materials include, but are not limited to, nickel, titanium, nickel-titanium alloys such as Nitinol, stainless steel, cobalt and chromium. The ceramics include, but are not limited to, silicon nitride, silicon carbide, zirconia, and alumina, as well as glass and silica, ePTFE (Expanded polytetrafluoroethylene) is a preferred substrate material for use in fabricating implantable devices of the present invention, and particularly for fabricating vascular grafts. Suitable ePTFE is available in the form of vascular grafts from such sources as IMPRA, Inc., Tempe, Ariz. Commercially available grafts are constructed of ePTFE and supplied in sterile form in a variety of configurations, including straight, tapered and stepped configurations.

Referring to FIG. 1, in the depicted embodiment, device 100 is stent, with an exterior surface 102a and an interior surface 102b which lines the lumen of the stent, both of which have reduced thrombogenicity meaning that they have a reduced tendency to promote, induce or facilitate formation of thrombi when in contact with bodily fluid or tissue. In the case of a coronary stent, since surface 102b contacts blood, including platelets, it is particularly important that surface 102b be rendered less thrombogenic, as described herein.

Device 100, in one particular variation, may comprise a polymeric stent fabricated as disclosed in U.S. patent application Ser. No. 10/867,617 filed Jun. 15, 2004 (U.S. Pat. Pub. 2005/0021131 A1), which is incorporated herein by reference in its entirety. The stent, as shown and described, may comprise a polymer that is at least partially amorphous and which undergoes a transition from a pliable, elastic state at a first higher temperature to a brittle glass-like state at a second lower temperature as it transitions through a particular glass transition temperature. This particular stent may be comprised of at least a first layer and a second layer where the first layer includes a first polymer that is at least partially amorphous and a second layer that is also at least partially amorphous. The stent may be formed to have a first shape at a relatively lower temperature and a second shape at a relatively higher temperature. The inner and/or outer layer of the stent 100 may be processed to have nano-crater 104 as described herein.

A substantially uniform layer of nano-craters 104 are distributed on surface 102a and 102b, meaning that nano-craters 104 of substantially similar depth are distributed on the surfaces 102a and 102b to form a discernible layer having such nano-craters. It has advantageously been found that the provision of such nano-craters 104 enhances endothelialization of surface 102a and 102b, resulting in reduced thrombogenicity. The stent 100 is suitable for long-term implantation in the body of a subject.

As used herein, the term "nano-crater" means indentations or depressions provided on a surface. Generally the indentations are on the nanometer scale. In different embodiments, the nano-craters have an average diameter of between about 30 nm and about 150 nm.

The stent 100 has nano-craters 104 sufficiently distributed over surfaces 102a and 102b to promote or enhance endothelialization, preferably over the entirety of surface 102a and 102b. The nano-craters 104 may be regularly or irregularly distributed over surfaces 102a and 102b. In some embodiments, adjacent craters may be spaced about 200 nm or greater apart.

Such nano-craters 104 may be suitably shaped, having a regular or irregular shape, provide that endothelialization of the surfaces 102a and 102b having the nano-craters 104 is enhanced and/or promoted. For example, the nano-craters 104 may be hemi-spherical, hemi-cylindrical or elliptical.

The size and shape of the nano-craters 104 can be controlled to provide a unique surface morphology. By varying this surface morphology, the range of sizes that selectively promote endothelial cell attachment while not being reception to platelet attachment, can be readily ascertained.

Optionally, surfaces 102a and 102b of the stent 100 can be chemically modified so as to further enhance or promote endothelialization, for example when implanted in a subject's body.

By way of background, it is noted that there are two ways by which an implanted device or surface can be covered with endothelial cells. In the first, called the transmural or capillary endothelialization, endothelial cells migrate into the device from tissue that is external to (usually above or below) the implanted device. For this sort of endothelialization to occur, the device itself must be sufficiently porous to permit the endothelial cells to migrate into it. A coronary stent such as the Palmaz stent (U.S. Pat. No. 6,379,383) is an example of such a device. This type of endothelialization may be achieved by coating an implantable device with a radiation-sensitive bioerodible polymer followed by irradiation with an electron beam to generate the nano-craters, as it set out below.

The second method of endothelialization involves migration of endothelial cells longitudinally into the device (e.g., in the lumen of a stent implanted in a blood vessel) from tissue adjacent to the device. In this case, porosity of the implantable device is not required, as endothelial cell attachment occurs from within a lumen or cavity of the device. However, the number of endothelial cells that are capable of this type of attachment is lower than those that can be achieved by transmural endothelialization.

Hence, it is envisaged that while the nano-cratered surfaces will enhance selective endothelial cell attachment on non-porous devices, the production and attachment of these endothelial cells in vivo may be enhanced using certain growth-stimulating molecules and adhesion-promoting molecules.

As used herein, the term "growth-stimulating molecule" refers to a molecule that stimulates or induces the differentiation, growth and proliferation of endothelial cells. Growth-stimulating molecules include peptides, proteins and glycoproteins, including hormones, capable of inducing an endothelial cell to grow and divide.

As used herein, the term "adhesion-promoting molecule" refers to a molecule that promotes or encourages adhesion or attachment of an endothelial cell to a surface. Adhesion-promoting molecules include peptides, proteins and glycoproteins capable of binding a cell to a substrate or to an adjacent cell.

As such, according to certain embodiments, surfaces 102a and 102b of the stent 100 include growth-stimulating molecules and/or adhesion-promoting molecules dispersed therein, which facilitate enhanced production of endothelial cells and their attachment to the nano-cratered surfaces 102a and 102b.

Suitable growth-stimulating molecules include granulocyte colony stimulating factor (gCSF), platelet-derived endothelial cell growth factor (PD-ECGF), fibroblast-derived endothelial cell growth factor alpha, endothelial cell growth factor beta, endothelial cell growth factor 2a and endothelial call growth factor 2b.

Suitable adhesion molecules are described in U.S. Pat. No. 5,774,515, which is herein incorporated by references. They are typically large, naturally occurring proteins or carbohydrates, with molecular weights above 100,000 daltons. In vivo, adhesion molecules are typically able to bind to specific cell surface receptors, and mechanically attached cells to the substrate or to adjacent cells. In addition to promoting cell attachment, suitable adhesion molecules can promote other cell responses including cell migration and cell differentiation (which in turn can include the formation of capillary tubes by endothelial cells).

Preferred adhesion molecules include substrate adhesion molecules (SAM's) such as the proteins laminin, fibronectin, collagen, vitronectin, and tenascin, and adhesion peptides or functional synthetic analogs derived from SAM's. Other suitable adhesion molecules include cell-to-cell adhesion molecules (CAM's) such as N-cadherin and P-cadherin.

Parent (i.e., native) adhesion proteins typically have one or more active peptide domains that bind to cell surface receptors and which domains produce the cell attachment, migration, and differentiation effects of the parent adhesion proteins. These domains consist of specific amino acid sequences, several of which have been synthesized and reported to promote the adhesion of endothelial cells. These domains and functional analogs of these domains are termed "adhesion peptides". In different embodiments, adhesion molecules are adhesion peptides and desirably, adhesion peptides have about 3 to about 30 amino acid residues in their amino acid sequences.

Adhesion peptides from fibronectin include, but are not limited to, RGD (arg-gly-asp) [SEQ ID NO.:1], REDV (arg-glu-asp-val) [SEQ ID NO.:2], and C/H—V (WQPPRARI or trp-gln-pro-pro-arg-ala-arg-ile) [SEQ ID NO.:3]. Adhesion peptides from laminin include, but are not limited to, YIGSR (tyr-ile-gly-ser-arg) [SEQ ID NO.:4] and SIKVAV (ser-ile-lys-val-ala-val) [SEQ ID NO.:5] and F-9 (RYVVL-PRPVCFEKGMNYTVR or arg-tyr-val-val-leu-pro-arg-pro-val-cys-phe-glu-lys-gly-met-asn-tyr-thr-val-arg) [SEQ ID NO.:6]. Adhesion peptides from type IV collagen include, but are not limited to, Hep-III (GEFYFDLRLKGDK or gly-glu-phe-tyr-phe-asp-leu-arg-leu-lys-gly-asp-lys) [SEQ ID NO.: 7].

While it is believed that nano-craters can selectively promote endothelialization, it is possible that platelet attachment to the nano-cratered surface may also be enhanced, leading to the undesirable effect of clot formation. To minimize any such effect, an anti-thrombotic molecule may be included on the surfaces 102a and 102b of the stent 100 by any suitable means, in amounts sufficient to minimize any platelet attachment during the process of endothelialization.

As used herein, an "anti-thrombotic molecule" is a molecule that reduces or prevents the formation of thrombi or clots on the surface of an implantable device that contacts bodily fluid or tissue, including when implanted in a subject's body. Anti-thrombotic molecules include, without limitation, heparin, and small molecules, such as benzamidine compounds, bicyclic pyrimidine compounds, nitro compounds, thio acid compounds, and proteins and peptides, including tissue-type plaminogen activator (t-PA), protein S and protein C.

The implantable device may be formed entirely from a single material and standard methods know in the art may be used to fashion the device. For example, a mold may be used, and a liquid polymer may be poured into the mold. This methods used will depend on the particular material used and the particular medical device that is to be formed.

In the case of the stent 100, the device may be formed by rolling a sheet or film of material, or by winding a thin strip of material into a helix, as is known in the art. In this way, the nano-craters may be readily formed on each side of the sheet or strip, as discussed below, prior to rolling or winding to form the stent.

The implantable device may also be formed from a substrate material and another material applied to the substrate material to form a bodily fluid or tissue contracting surface by any suitable means, for example, by spin-coating from a solution or suspension, and the nano-craters are subsequently introduced into the surface. This surface layer should have sufficient thickness to introduce nano-craters having depth sufficient to enhance or promote endothelialization.

Without intending to particularly limit the method by which the nano-craters 104 are introduced to the surfaces 102a and 102b of the stent 100, the following illustration of two possible approaches for forming the nano-craters 104 are provided.

Figure 2:
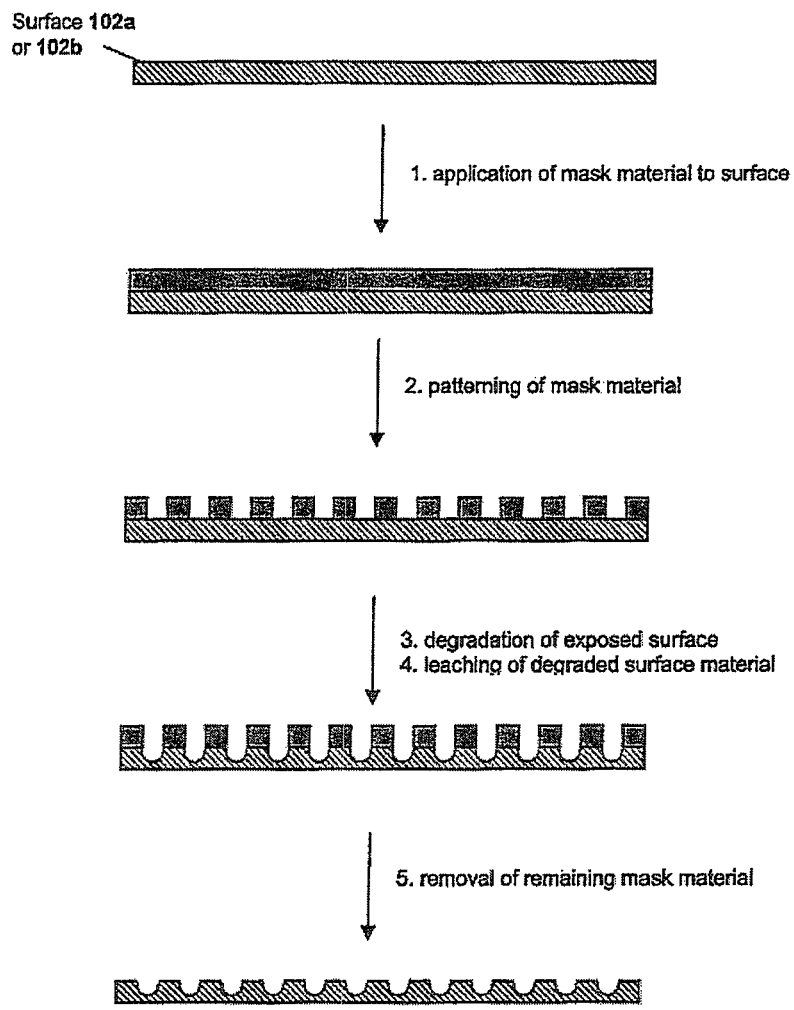
FIG. 2 is a Schematic diagram of a process to form nano-craters in a surface using a mask and etching techniques.

The nano-craters 104 may be introduced through controlled degradation of the surfaces 102a and 102b of the stent 100, as depicted in FIG. 2. According to this approach, discrete portions of surfaces 102a and 102b, both of which are formed from a degradable polymer, are etched using a degradative process, for example, by exposing the polymer surface to electron beam radiation or by treating with a chemical that will degrade the surface, for example, strong alkali.

The technique of masking certain areas of the surface 102a and 102b may be employed to define areas of degradation. A higher density material, for example a silicon-based polymer or an acrylic polymer, may be patterned over surface 102a and 102b in which the nano-craters 104 are to be introduced, in a pattern that defines the desired distribution and depth of the nano-craters. For example, a focused ion beam may be used to form the desired pattern in the mask material which is layered on the degradable surface 102a and 102b.

After exposure to the etching means that degrade the unmasked regions of surface 102a and 102b, for example radiation or chemical means, the surface material in the degraded areas may then be leached out using water or solvent in which the degraded portions of the surface material are soluble, but which will not dissolve the non-degraded regions of the surface. The mask material may then be subsequently removed, for example by dissolution in a suitable solvent that dissolves the mask material but not the polymer surface 102a and 102b.

To illustrate, in one example, PLGA, PLLA, PGA, polycaprolactone or polyethylene may be employed to form the stent 100 or surfaces 102a and 102b of the stent 100, both of which degrade in the dry state under electron-beam irradiation.

Thus, the degree of degradation may be controlled using the well-known effects of attenuation with depths of an incident electron beam. The depth of penetration of the incident electron beam is generally proportional to the electron energy or the accelerating voltage being used. This depth-dose distribution is determined by the absorption mechanism of mono-energetic electron beams having electron energy, eV, for a material of density p. The higher the density of a given material, the grater the attenuation effect on the electron beam. This attenuation effect will result in a varying radiation dose across the thickness of the surface and patterned higher density material, resulting in a variation of molecular weight of the polymer across the thickness of the surface.

An example of utilizing an incident electron beam for patterning a surface of a polymeric sample may include use of electron beam lithography, which is typically used in the semiconductor electronics industry for patterning integrated circuits and biosensors. Generally, a polymeric substrate having a radiation-sensitive film or resist may be placed in a vacuum chamber of a scanning-electron microscope and exposed by an electron beam under digital control. Because the beam width may be adjusted to range from a few picometers to several nanometers, an etched pattern may be formed by the beam across the polymer surface.

This variation of molecular weight across the thickness of the surface will result in differing degradation rates at areas masked with the higher density material than those not asked. When these non-masked degraded sections are exposed to water (or another suitable solvent), the leaching of low-molecular weight, water-soluble oligomers from the water-insoluble not-degraded regions of the surface will result in well-defined craters of known lateral dimensions and depth. Thus, the size and shape of the nano-craters 104 may be accurately controlled by this method, for example by controlling the does of the radiation, and the density of the material used to mask, as well as the pattern in which the masking material is applied. This results in a unique surface morphology, as discussed above, that selectively promotes endothelial cell attachment, while not being receptive to platelet attachment.

Alternatively, chemical means can be used with the above-described masking method to produce nano-craters at the surfaces 102*a* and 102*b*. For example, sodium hydroxide may be used to dissolve PLA in regions that are not protected by the alkali-resistant mask material, and the dissolved material may then be rinsed away in water to form nano-craters 104. The mask may be removed as described above.

The nano-craters 104 may alternatively be formed on the surfaces 102*a* and 102*b* of the stent 100 by including nano-particles that are leachable from the surfaces 102*a* and 102*b*.

A "nano-particle" is any granular or particulate material in which the particulates have dimensions in the nano-meter range. The nano-particles may be irregularly shaped, or may be of well-defined size and shape, and may be leached from the surface leaving behind nano-craters corresponding to the size and shape of the nano-particles.

The nano-particles may be formed of any granular or particulate material which can be embedded in the material used to form surface 102*a* and 102*b*, which will not dissolve in or become irreversibly bound to the material, and which can then be subsequently leached from the material. For example, the nano-particles can be formed from an inorganic salt, such as sodium chloride, form gelatin, sugar, chitosan, or polyvinyl pyrrolidone.

The nano-particles may be suspended in a dilute solution of a polymer being used to form the implantable device or more preferably, the surface of the implantable device which may then be spin-coated onto the substrate of the device at a desired thickness. The thickness will usually be in the micrometer range. By casting a very thin layer containing the nano-particles, it is possible to form a layer of polymer on an implantable device that has nano-craters only at the surface.

Subsequently, these particles on the surface are either leached out upon exposure to water or another suitable solvent, or are eroded once the device comes in contact with bodily fluid or tissue, for example when stent 100 is implanted, leaving behind a surface with well defined nano-craters 104 of know dimensions. Advantageously, the dimensions of the nano-craters 104 may be varied by varying the size and shape of the nano-particles dispersed in the polymer.

If the bodily fluid-contacting or tissue-contacting surface of the implantable device is to contain adhesion-promoting molecules, the nano-craters may be created, for example by irradiation, and concurrently the surface may be modified to release adhesion-promoting molecules and/or growth-stimulating molecules, for example into a lumen or cavity of the implantable device. The adhesion-promoting molecules and/or growth-stimulating molecules may be passed to a polymer used to form the implantable device or the surface of the implantable device prior to coating the polymer on the substrate of the implantable device, and forming nano-craters.

However, adhesion-promoting molecules and growth-stimulating molecules may typically be proteins, which are sensitive biomolecules that may be denatured by addition to a liquid polymer, or when subjected to high intensity radiation. Thus, the adhesion-promoting molecules and/or growth-stimulating molecules may first be encapsulated in nano-particles of well-defined size and shape as it known in the art, for example, as described in U.S. Pat. No. 6,589,562 which is herein fully incorporated by reference. The nano-particles may be leached out as discussed above, leaving behind the nano-craters and simultaneously releasing the adhesion-promoting molecules and/or growth-stimulating molecules, for example into a lumen. The nano-particles, when containing adhesion-promoting molecules and/or growth-stimulating molecules for delivery to bodily fluid or tissue comprise a material that is soluble in bodily fluid or tissue, for example, gelatin.

An anti-thrombotic molecule may be included in the nano-crated surface of an implantable device in a similar manner.

In an alternative embodiment, an implantable device with reduced thrombogenicity is achieved by providing the device with a surface that will degrade in a layered fashion when it contacts bodily fluid or tissue. This embodiment is useful for applications in which the device will be in contact with bodily fluid or tissue for a relatively short period of time, for example, a catheter or dialysis tubing that is in such contact for less than 24 hours. Preferably, the layers degrade relatively quickly, so as to prevent the formation of thrombi. This means that the degradation time for a given layer upon contacting bodily fluid or tissue may be, for example, between about 5 minutes and about 1 hour.

Figure 3:
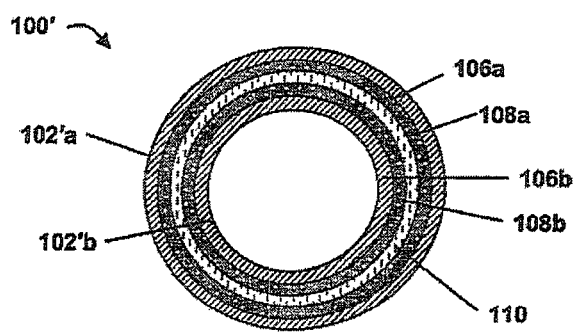
FIG. 3 is a schematic representation of an implantable device having two degradable layers.

Thus, with reference to FIG. 3, in an illustrative embodiment, a stent 100' has first degradable layers 106*a* and 106*b* disposed about a central core 110, and which layers provide surfaces 102'*a* and 102'*b* that comes into contact with bodily fluid or tissue, including blood, and second degradable layers 108*a* and 108*b*, between layers 106*a* and 106*b*, respectively, and the central core 110 of stent 100'. In the depicted embodiment, the stent 100' has a first surface 102'*a*, which forms the exterior surface of the stent and an interior surface 102'*b* which defines the lumen of the stent.

The second degradable layers 108*a* and 108*b* are the inner layer relative to the outer surfaces 102*a*' and 102'*b*, respectively, and have a slower degradation rate than the first degradable layers 106*a* and 106*b*. Therefore, on contact with bodily fluid or tissue, there is a peeling effect resulting from successive degradation of first degradable layers 106*a* and 106*b* followed by degradation of the second degradable layers 108*a* and 108*b*, and any thrombus formation on surface 102'*a* and 102'*b* is removed as the layers erode.

As mentioned above, the stent 100' may also be configured and comprised in the manner as shown and described in U.S. patent application Ser. No. 10/867,617, which has been incorporated above by reference in its entirety. In one variation, the stent 100' configured as disclosed in U.S. patent application Ser. No. 10/867,617 may comprise the central core 110 having the multiple degradable layers disposed thereon. In other variations, it may be possible to have the multiple degradable layers correspond to the multiple layers comprising the stent structure.

The degradable layers 106a and 106b and 108a and 108b may be formed from any biodegradable polymers that are generally known in the art and described above and hereafter. For example, suitable polymers include polylactic acid (PLA) and polyglycolic acid (PGA) and copolymers of PLA and PGA (PLGA). These polymers may be amorphous or semi-crystalline.

For example, in one embodiment layers 106a and 106b may comprise PLA and the layers 108a and 108b may comprise PLGA, particularly PLDA 80/20; PLGA 75/25; or PLGA 53/47, wherein the numbers in the copolymer represent the percentage of PLA and PGA by weight, respectively, included in the copolymer.

Preferably, the thickness of each layers 106a and 106b and 108a and 108b is in the micrometer or sub-micrometer range, for example about 0.5 µm to about 10 µm.

In stent 100', the central core 110 may comprise a different material than layers 106a, 106b, 108a and 108b, and the material comprising the respective layers may be applied to central core 110. Alternatively, stent 100' may be formed of a single polymeric material but having first and second degradable layers of different average molecular weights of the polymer than found in central core 110, so as to form the discrete layer 106a, 106b, 108a, and 108b about central core 110, as described below.

Without intending to particularly limit the method by which the degradable layers 106a and 106b and 108a and 108b having varying degradation rates are provided on the central core 110, the following illustration of two possible approaches for forming the degradable layers are provided.

Polymers having different degradation rates can be selected and applied successively such that the layers 108a and 108b comprise a polymer with a slower degradation rate. A polymer with a faster degradation rate is selected for layers 106a and 106b such that layer 106a and 106b degrade more rapidly and remove any thrombus that may have formed on the surfaces 102'a and 102'b, respectively.

A skilled person will appreciate that a layered device having first and second degradable layers may comprise additional degradable layers, and that the degradation rate of each degradable layer increases with each successively inward layer such that the outer-most layer degrades more quickly and that the inner-most layer degrades most slowly. For example, in one particular embodiment, a layered device may comprise the following layers disposed about a central core: PLA; PLGA 80/20; PLGA 75/25; and PLGA 53/47 in the given order with PLGA 53/47 being the outer-most layer.

The suitable number of layers to be applied can be readily determined and will depend on the degradation rates of the layers and the particular type of device and its intended use, including the intended duration of contact with bodily fluid or tissue.

Each of such layers may be spin-coated or solvent cast on to a substrate material forming the implantable device, using a solution or suspension containing, for example, about 10 to about 40% polymer by weight. As will be appreciated, other suitable means of applying thin layers of a polymer to a substrate may also be employed, for example, vapour deposition.

Alternatively, controlled degradation of a surface of an implantable device may be effected, for example, using radiation such as electron beam radiation. This method utilizes the attenuation effect of electron beam radiation within an irradiated material.

To illustrate, a single biodegradable material may be applied to the surface of an implantable device as described above and then irradiated to provide layers having different average molecular weights of the biodegradable material, and therefore varying degradation rates.

The suitable thickness of the material to be applied will typically be in the micrometer range, for example about 1 micron to about 20 microns, and can be readily determined. The desired thickness will depend on the particular polymer used and on the particular type of device and its intended use, including the intended duration of contact with bodily fluid and tissue.

The mechanism of attenuation, as discussed above, can be described as the loss of energy of the accelerating electrons. The depth of penetration is proportional to the electron energy or the accelerating voltage, and is attenuated in a manner proportional to the density of the material being penetrated. This attenuation effect will result in a varying radiation does through the depth of the material as the beam is attenuated as it travels deeper into the material, with the exterior surface receiving the strongest does of radiation. This will result in a variation of molecular weight in the surface material as a function of penetration depth or material thickness. This variation of molecular weight through the depth of the material will in turn result in different degradation rates of the material coated on the device, thereby providing the first degradable layer, which due to the higher radiation does will have a lower molecular weight and will degrade faster then the underlying second degradable layer. This will result in a 'layer peeling' effect across the thickness of the polymer when in contact with bodily fluid or tissue.

The above-described devices can provide an implantable device having reduced thrombogenicity on contact with bodily fluid or tissue, for example when implanted, as compared to that typically observed with implantable medical devices. Standard surgical methods for implanting medical devices are known in the art. The method of implantation and duration of implantation will depend on the type of implantable device used, for example, a stent or a valve, the purpose of implantation and the disorder or condition that is to be treated with the implantable medical device. Thus, a method for reducing thrombogenicity, and for enhancing or promoting endothelialization, of an implantable device having at least one surface for contacting bodily fluid or tissue is contemplated.

The method comprises providing on the at least one surface a plurality of nano-craters that enhance or promote endothelialization of the at least one surface.

Alternatively the method comprises providing at least one first degradable layer which provides said at least one surface and which is disposed about a central core, and at least one second degradable layer between said first degradable layer and the central core, wherein said first degradable layer has a first degradation rate and said second degradable layer has a second degradation rate such that said at least one first degradable layer degrades more rapidly then said at least one second degradable layer so as to remove any thrombus that may be formed on said at least one surface.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of know equivalents for any aspect of the invention in order to achieve the same result in substantially the same way. All technical and scientific terms used herein have the same meaning as commonly understood by one of ordinary skill in the art of this invention, unless defined otherwise.

Example 1

For the following examples, each polymer was first dissolved in chloroform. Nano-sized salt particles were ground and sieved, and then dispersed in the polymer solution with constant stirring until the particles were visually uniformly dispersed. The polymer concentration was chosen such that it had sufficiently high viscosity to maintain a stable dispersion. The dispersion was then cast as a film of required thickness using a coater. The film was dried in an oven at 37° C., and then left at room temperature for several days in a dry environment. The dried films were immersed in water for 14 days, with constant exchange of the water. The salt nano-particles were thus leached out, and the resulting film was dried again at 37° C. and at room temperature.

Control films were prepared as pure polymer films without any surface modification.

PLLA and PLGL films having nano-craters in the surface were obtained by leaching out incorporated nano-particles of NaCl, as indicated in Table 1.

The best result were obtained with PLLA polymer surfaces prepared by incorporation and leaching out of salt particles (<90 Micron Diameter). Rapid endothelial cell attachment was seen with these surfaces, with significant coverage of the surface by cells.

Although early attachment of cells to the PLGA polymer film was observed, the results obtained with PLGA did not result in significant endothelialization of the polymer film. This is likely due to the molecular weight of PLGA chosen, or the ratio of lactide to glycolide in the copolymer, resulting in a polymer that degraded under the conditions used to leach the salt particles, and confirms that the degradation properties of the polymer and dissolution rate of the leachable salt particle can affect the formation of nano-craters. The resulting craters were therefore likely too large and improperly formed to promote confluent growth and attachment of the cells. This problem can be solved by varying the PLGA used to select a more stable form of PLGA and to increase the rate of leaching of salt particles, such that the PLGA is not degraded during the leaching process.

TABLE 1

Results of Endothelialization of Nano-Cratered Surfaces.

| Material | Sample Preparation | Surface Treatment | Cell Seeding (cells/sq cm) | First endothrlial call attachment | Result at days 4/5 |
|---|---|---|---|---|---|
| Control PLLA | Polymer + Solvent PLLA | NIL | 20000 | 36 hours | Day 5 approximately 20% confluency |
| Contold PLGA | Polymer + Solvent PLGA 80:20 | NIL | As Above | 36 hours | Day 5 approximately 40% confluency |
| PLLA with Nanocraters | Polymer + Solvent PLLA | Leached NaCl 99% purity <90 Microns 1% concentration Leaching period 15 days. | As Above | 2 hours | At Day 4 about 70% confluency Seen. |
| PLGA with nanocraters | Polymer + Solvent PLGA 80:20 | Leached NaCl 990% Purity <90 microns 1% concentration Leaching period 15 days. | As Above | 6 hours | At Day 4 about 5% confluency Seen. |

Example 2

In another example of a method for modifying a surface of a polymer for implantation within a patient body, porogen leaching of surfaces may be utilized to yield a surface which enhances endothelial cell growth over a defined range of surface features. In this particular example, surface pores were created by filling polymers such as Poly caprolactone (PCL), Poly L-lactide (PLLA), Poly (lactide-co-glycolide), etc. (although any of the other suitable polymers described herein may be utilized) with leaching agents of sugar and gelatin.

The sugar and gelatin particles ranged in size from 20 to 90 microns in diameter (although particles as small as 5 microns may also be utilized) where the average particle sizes typically ranged from 20, 45, and 90 microns. The leaching agents were added in concentrations ranging from 1 to 10% by weight in the polymer. More particularly, the leaching agents were added in concentrations ranging from 1%, 5%, and 10% by weight in the polymer.

The leaching agents were then leached out with water from the polymer for a period of 10 to 12 days and the surface porosity was characterized by a scanning electron microscope (SEM) for crater dimensions and inter-crater spacing. With the physical characteristics determined, the surfaces of the polymer were then exposed to endothelial cells over an 11 day period, at the end of which the cells attached to the surface were counted and correlated to the surface features.

Figure 4:
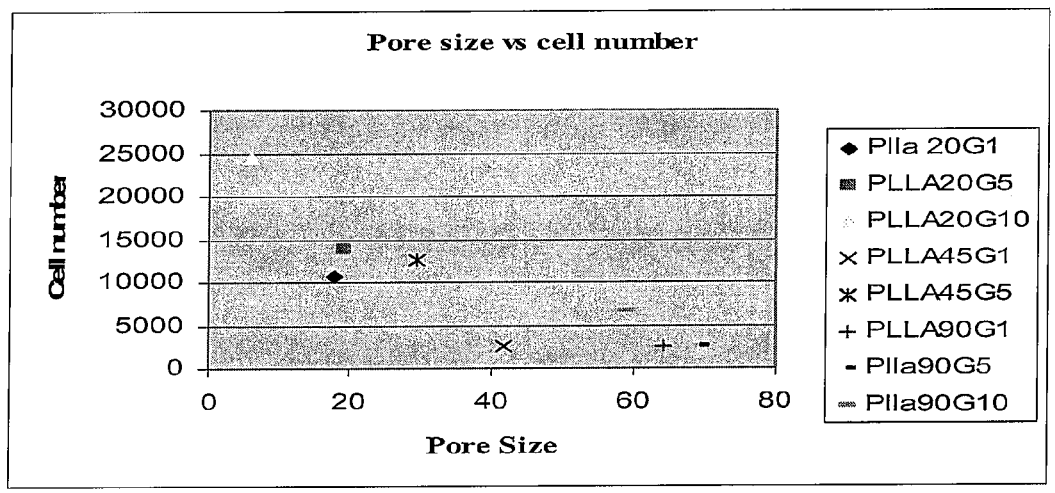
FIG. 4 illustrates some of the results of the number of cells correlated to pore size in a PLLA polymer.
Figure 5:
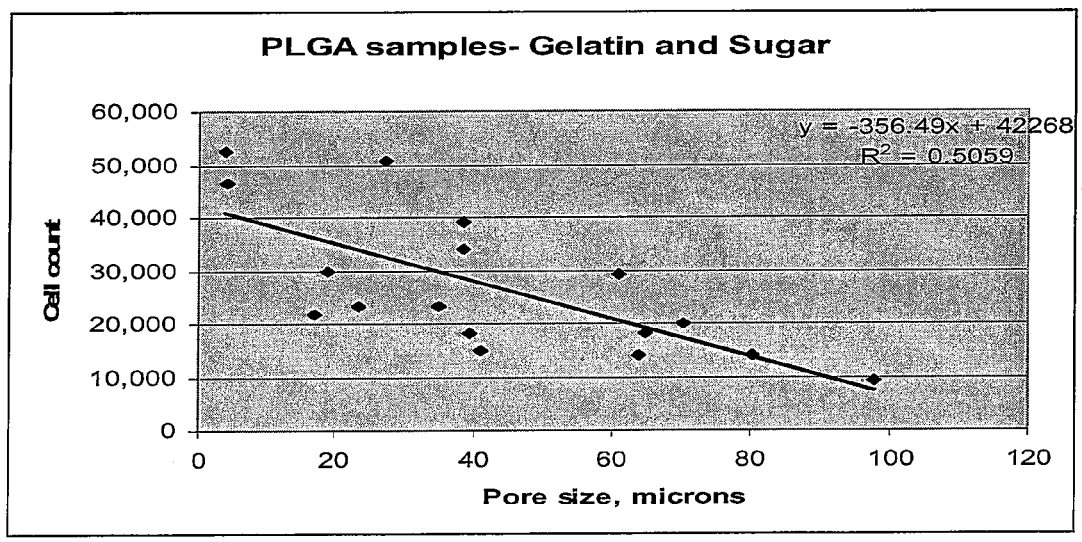
FIG. 5 also illustrates some of the results of the number of cells correlated to pore size in a PLGA polymer sample.

FIG. 4 illustrates some of the results of the number of cells correlated to pore size in a PLLA polymer sample at day 9, which is representative of the results. FIG. 5 also illustrates some of the results of the number of cells correlated to pore size in a PLGA polymer sample (specifically PLGA 80/20) also at day 9. In both the PLLA and PLGA polymers, each sample was prepared utilizing the methods described above. Generally, endothelial cell growth appeared better on PLGA 80/20 samples than on PLLA samples. Moreover, both gelatin and sugar pyrogens appear to act similarly and regardless of the porogen used, cell growth appears inversely dependent on pore size. However, gelatin appeared to be optimal for use as a porogen in the size range of about 5 to 40 microns at concentrations of about 5 to 10% in the starting solution. The PCL samples, also prepared as described above, showed growth of endothelial cells although the growth did not appear dependent on pore size in the range studied.

Generally, endothelial cell attachment and proliferation is higher at lower crater sizes (between about 5-10 microns) and decreases with higher crater size up to about 90 microns; however, compared to controls (no craters), all the samples showed enhanced endothelial cell attachment.

Figure 6:
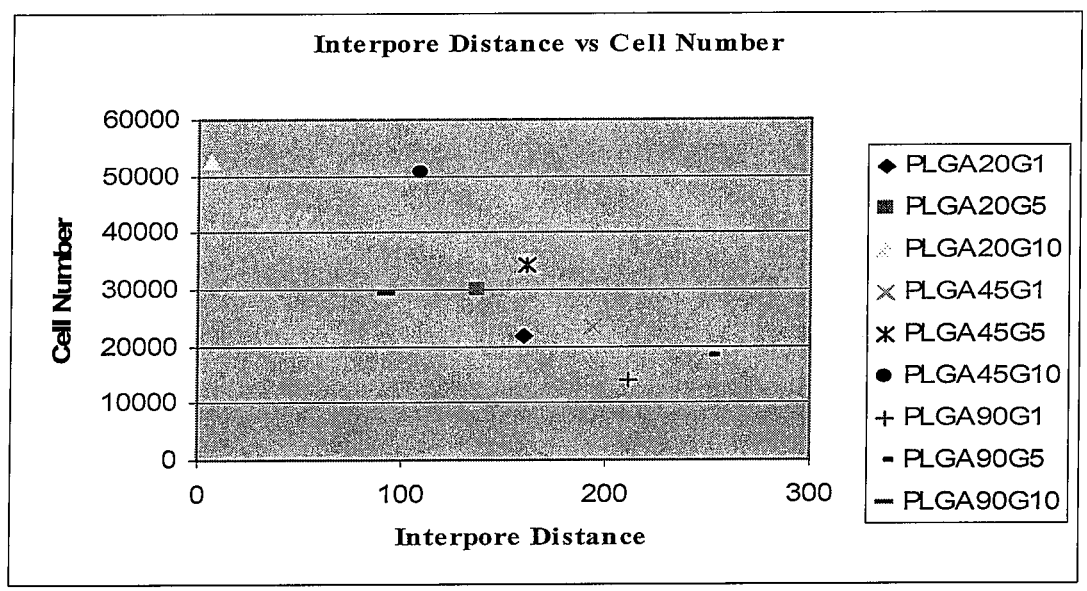
FIG. 6 illustrates results correlating inter-pore distance to cell attachment and growth of the endothelial cells.

By changing the concentration of the particles in the polymer (prior to leaching), mentioned above as 1%, 5%, and 10% concentrations, the inter-pore distances along the polymer surfaces were varied from an average of about 50 microns to 250 microns. As illustrated by the results in FIG. 6, an inter-pore distance ranging from about 50 to 100 microns and more preferably between 50 to 80 microns appeared optimal for attachment and growth of the endothelial cells.

Accordingly, endothelial cell growth appears to correlate inversely to pore size on surfaces of PLLA and PLGA samples, but not to PCL samples. As pore size is decreased (e.g., down to about 5 to 10 microns), endothelial cell growth is increased. However, at all pore sizes, PCL showed good endothelial cell growth on its surface.

Example 3

As mentioned above, chemicals such as sodium hydroxide may be used to dissolve PLA in regions unprotected by an alkali-resistant mask material where the dissolved material may be rinsed away in water to form nano-craters. In another example, the polymer surface may be first irradiated prior to etching with the sodium hydroxide to enhance the etching process.

In this example, samples of PLGA, PCL, and PLLA (other suitable polymers described above may alternatively be utilized) were first irradiated with an electron beam and then etched using the sodium hydroxide, as described above, for a period of 16 hours to create surface features. The average surface roughness of the samples was measured using an atomic force microscope (AFM) and the etched samples were then exposed to endothelial cells. Growth was quantified over a period of 15 days and the irradiated and etched samples were compared to control samples after 4 days, 8 days, and 15 days. Table 2 shows a comparison of the results for sample roughness between the irradiated and control samples where the MTS value is an indication of the number of active cells.

TABLE 2

Results of Comparison For Irradiated and Control Samples With Respect to Sample Roughness and Cell Growth.

|  | AFM Avg surface Roughness (Scan Size 50 μm) | Static Contact Angle | MTS Average Absorbance after 4 days | MTS Average Absorbance after 8 days | MTS Average Absorbance after 15 days |
|---|---|---|---|---|---|
| PLGA Control | 3.3 ± 1 | 7.32 ± 1 | 0.51 | 0.37 | 0.26 |
| PLGA Modified | 93 ± 3 | 57.4 ± 2 | 0.57 | 0.29 | 0.45 |
| PLLA Control | 646 ± 9 | 94.2 ± 2 | 0.40 | 0.29 | 0.40 |
| PLLA Modified | 333 ± 27 | 63.4 ± 1 | 0.51 | 0.17 | 0.27 |
| PCL Control | 259 ± 20 | 80.2 ± 3 | 0.39 | 0.24 | 0.28 |
| PCL Modified | 390 ± 16 | 61.8 ± 1 | 0.53 | 0.38 | 0.39 |

*Modified = Ebeam with 2.5 Mrads + 16 hours 0.1N NaOH immersion

Generally, irradiating samples prior to etching with sodium hydroxide gives surface features that are rougher than control samples. Table 3 shows a comparison of the results for the irradiated and control samples with respect to live cell growth and total cell growth.

TABLE 3

Results of Comparison For Irradiated and Control Samples With Respect to Live Cell Growth and Total Cell Growth.

|  | Hemocytometer Avg Live Cells Count after 4 day | Hemocytometer Avg total Cells Count after 4 day | Hemocytometer Avg Live Cells Count after 8 day | Hemocytometer Avg total Cells Count after 8 day | Hemocytometer Avg Live Cells Count after 15 day | Hemocytometer Avg total Cells Count after 15 day |
|---|---|---|---|---|---|---|
| PLGA Control | 5400 | 9600 | 9300 | 15800 | 9400 | 22700 |
| PLGA Modified | 8800 | 12800 | 9700 | 17800 | 17800 | 31400 |
| PLLA Control | 5300 | 9000 | 3800 | 4900 | 13500 | 27700 |
| PLLA Modified | 6500 | 8800 | 3300 | 4800 | 13600 | 27400 |
| PCL Control | 4400 | 9200 | 1530 | 3800 | 3060 | 12000 |
| PCL Modified | 4100 | 7600 | 9830 | 14200 | 5300 | 23400 |

*Modified = Ebeam with 2.5 Mrads + 16 hours 0.1N NaOH immersion

Generally, the surface-modified samples show enhanced endothelial cell growth for PLGA and PCL samples except for PLLA samples. The endothelial cell growth also appeared to correlate well with overall surface roughness of PLGA and PCL samples where endothelial cell growth increases as surface roughness increases.

As can be understood by one skilled in the art, many modifications to the exemplary embodiments described herein are possible. The invention, rather, is intended to encompass all such modification within its scope, as defined by the claims.

What is claimed is:

1. An implantable device comprising:
   a central core defining a lumen through said core with an inner core surface along said lumen and an outer core surface;
   at least one first degradable layer formed upon said inner core surface and said outer core surface for contacting bodily fluid or tissue, wherein the first degradable layer comprises a polymer selected from the group consisting of PLGA 80/20, PLGA 75/25, and PLGA 53/47; and
   at least one second degradable layer formed between said inner core surface and said first degradable layer and also between said outer core surface and said first degradable layer, wherein said first degradable layer has a first degradation rate and said second degradable layer has a second degradation rate such that said at least one first degradable layer degrades more rapidly than said at least one second degradable layer on contact with bodily fluid or tissue.

2. The implantable device of claim 1, wherein the first degradable layer comprises a different material from the second degradable layer.

3. The implantable device of claim 1, wherein the second degradable layer comprises poly-lactide (PLA) and the first degradable layer comprises poly(lactide-co-glycolide) (PLGA).

4. The implantable device of claim 1, further comprising:
   at least one third degradable layer between the at least one second degradable layer and the central core and having a third degradation rate slower than the second degradation rate; and
   at least one fourth degradable layer between the at least one third degradable layer and the central core and having a fourth degradation rate slower than the third degradation rate.

5. The implantable device of claim 4, wherein the first degradable layer comprises PLGA 53/47, the second degradable layer comprises PLGA 75/25, the third degradable layer comprises PLGA 80/20, and the fourth degradable layer comprises PLA.

6. The implantable device of claim 1, wherein the implantable device is selected from the group consisting of a stent, a graft, a conduit, a valve, and a dialysis tubing.

\* \* \* \* \*